US010322022B2

(12) United States Patent
Jara

(10) Patent No.: US 10,322,022 B2
(45) Date of Patent: Jun. 18, 2019

(54) PLANTAR FASCIITIS TREATMENT METHOD AND DEVICE

(71) Applicant: Herminsul Jara, Miami, FL (US)

(72) Inventor: Herminsul Jara, Miami, FL (US)

(73) Assignee: J-FLEX PFT, LLC, Miami, FL (US)

( * ) Notice: Subject to any disclaimer, the term of this patent is extended or adjusted under 35 U.S.C. 154(b) by 570 days.

(21) Appl. No.: 14/944,623

(22) Filed: Nov. 18, 2015

(65) Prior Publication Data
US 2017/0135837 A1 May 18, 2017

(51) Int. Cl.
*A61F 5/01* (2006.01)
*A61F 5/37* (2006.01)
*A61F 5/042* (2006.01)
*A63B 21/055* (2006.01)
*A63B 21/00* (2006.01)
*A63B 23/10* (2006.01)
*A63B 23/035* (2006.01)
*A63B 21/04* (2006.01)

(52) U.S. Cl.
CPC ............ *A61F 5/0111* (2013.01); *A61F 5/042* (2013.01); *A61F 5/3715* (2013.01); *A63B 21/00185* (2013.01); *A63B 21/0552* (2013.01); *A63B 21/0557* (2013.01); *A63B 21/4009* (2015.10); *A63B 21/4011* (2015.10); *A63B 21/4015* (2015.10); *A63B 23/03508* (2013.01); *A63B 23/10* (2013.01); *A61F 2005/0197* (2013.01); *A63B 21/0442* (2013.01); *A63B 21/4034* (2015.10)

(58) Field of Classification Search
CPC .............................. A61F 5/0111; A61F 5/042; A61F 2005/0197; A63B 23/10; A63B 21/4015; A63B 21/4009; A63B 21/0552; A63B 21/4011
USPC .......................................................... 602/23
See application file for complete search history.

(56) References Cited

U.S. PATENT DOCUMENTS

| | | | | |
|---|---|---|---|---|
| 1,608,032 A | * | 11/1926 | McNabb | A61F 5/0104 602/30 |
| 4,252,112 A | * | 2/1981 | Joyce | A61F 5/0104 601/34 |
| 5,246,119 A | * | 9/1993 | Heffner | B07C 7/04 209/702 |
| 5,256,119 A | * | 10/1993 | Tudor | A63B 23/04 128/882 |
| 6,428,495 B1 | * | 8/2002 | Lynott | A61F 5/3715 128/875 |
| 7,041,074 B1 | * | 5/2006 | Averianov | A61F 5/0102 128/845 |

(Continued)

*Primary Examiner* — Tarla R Patel
(74) *Attorney, Agent, or Firm* — Dunlap Bennett & Ludwig PLLC

(57) ABSTRACT

A device for treatment of plantar fasciitis is provided. The device includes a foot strap, a thigh strap and a resistance band. The foot strap includes an inner surface and an outer surface. The inner surface of the foot strap is sized to secure around a foot of a user in between the ankle and toes. The thigh strap also includes an inner surface and an outer surface. The inner surface of the thigh strap is sized to secure around a thigh of the user. The resistance band includes a first end attached to the foot strap and a second end attached to the thigh strap. To treat the plantar fascia, the user bends their foot downwards and curls the toes against the resistance of the resistance band.

11 Claims, 4 Drawing Sheets

(56) References Cited

U.S. PATENT DOCUMENTS

| | | | |
|---|---|---|---|
| 7,175,604 B2* | 2/2007 | Cole ................... | A61F 5/0102 482/124 |
| 7,654,921 B2* | 2/2010 | Brunst ............... | A63B 69/0002 473/422 |
| 2008/0039303 A1* | 2/2008 | Wilcocks ........... | A63B 21/0552 482/124 |
| 2011/0160630 A1* | 6/2011 | Cerioli ................ | A61F 5/0111 602/23 |
| 2013/0231227 A1* | 9/2013 | Ranieri ............. | A63B 21/0421 482/124 |

* cited by examiner

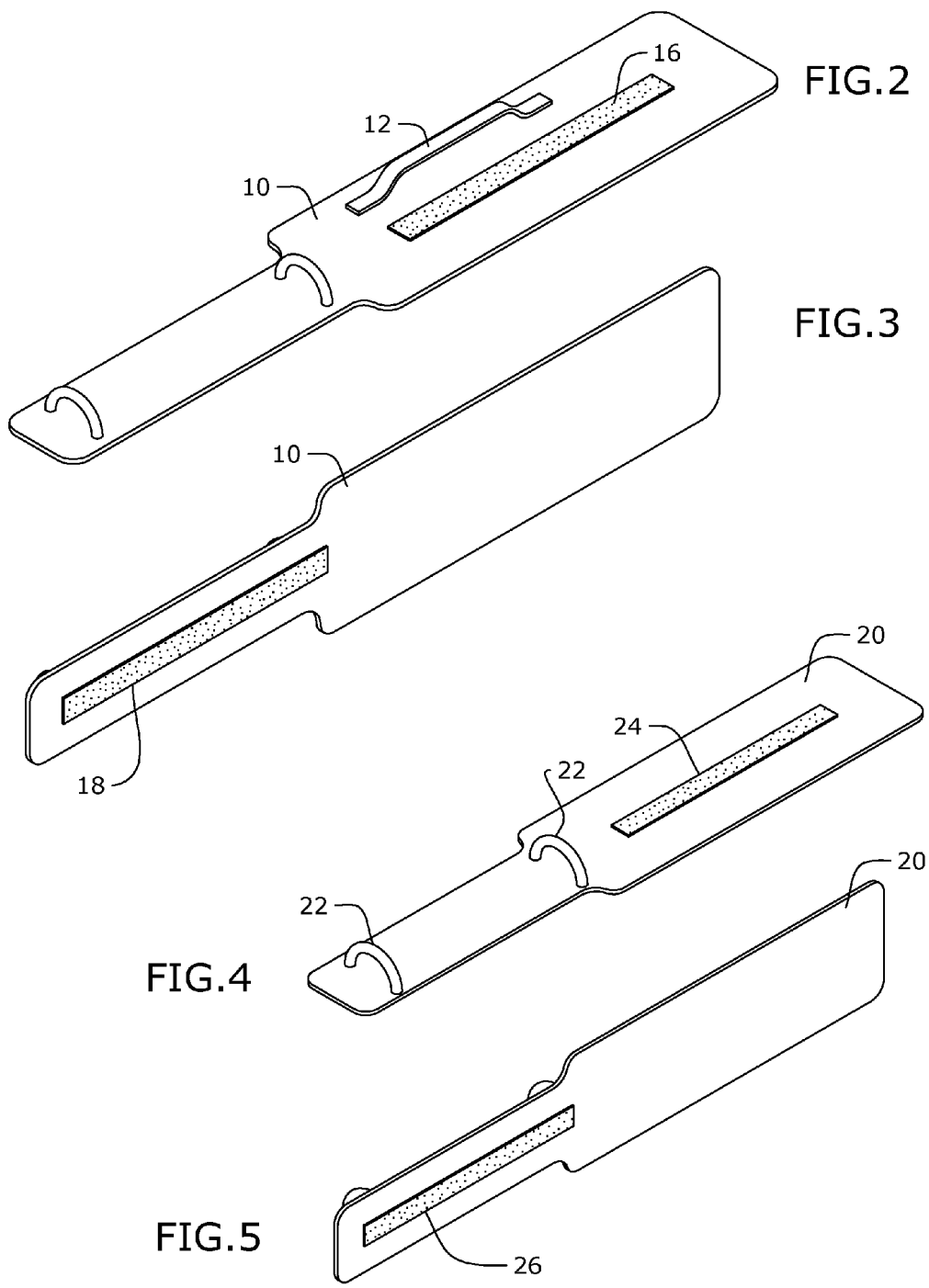

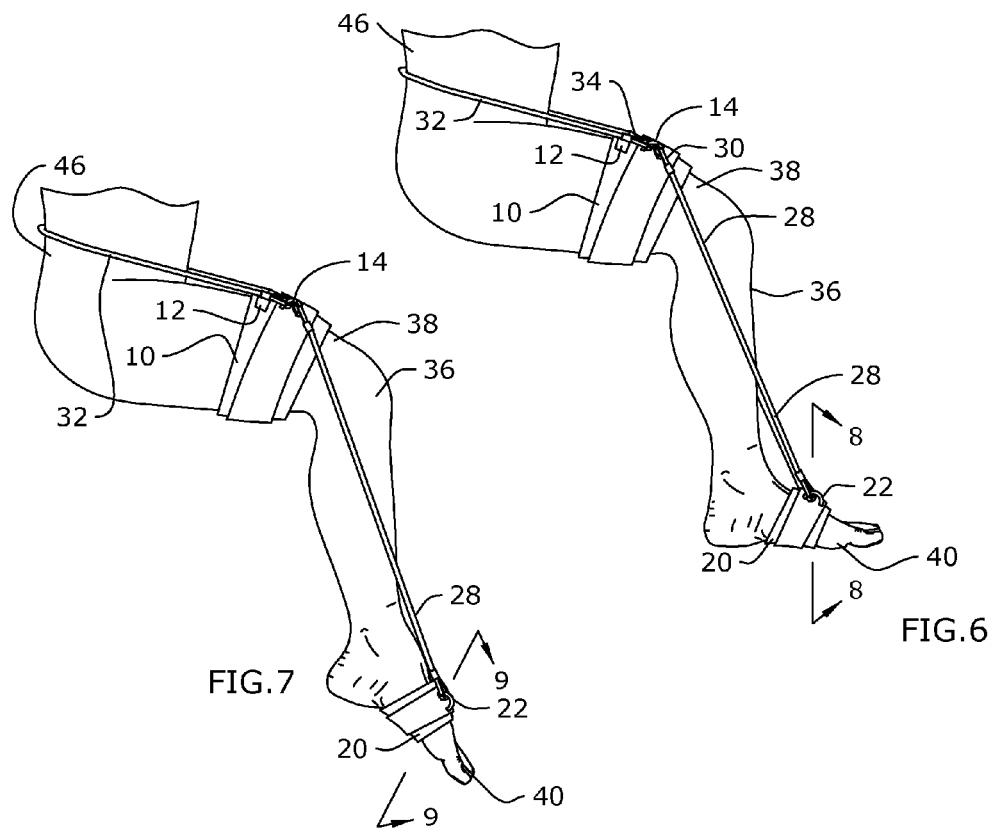
FIG.6
FIG.7
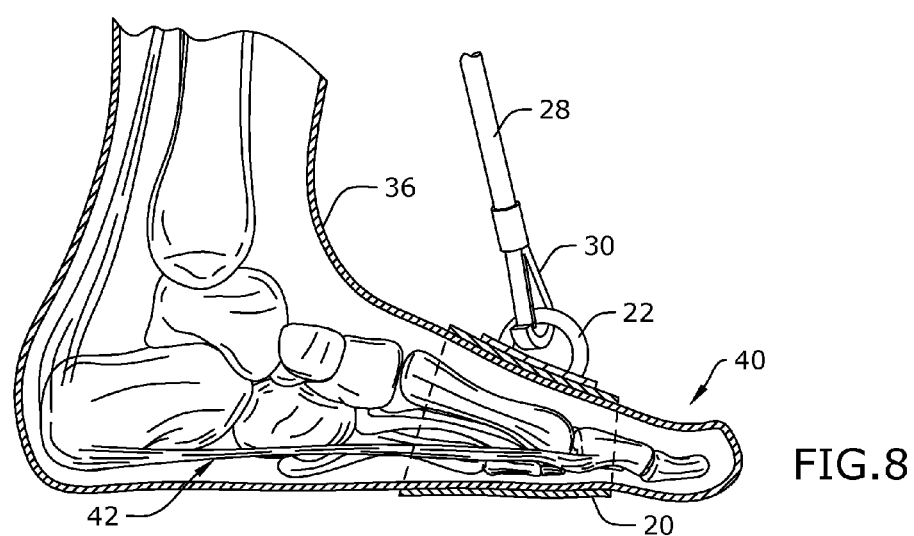
FIG.8

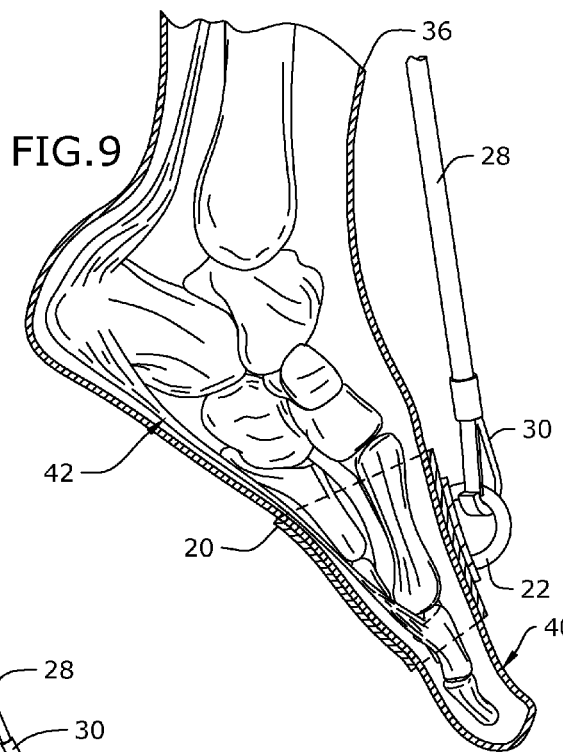
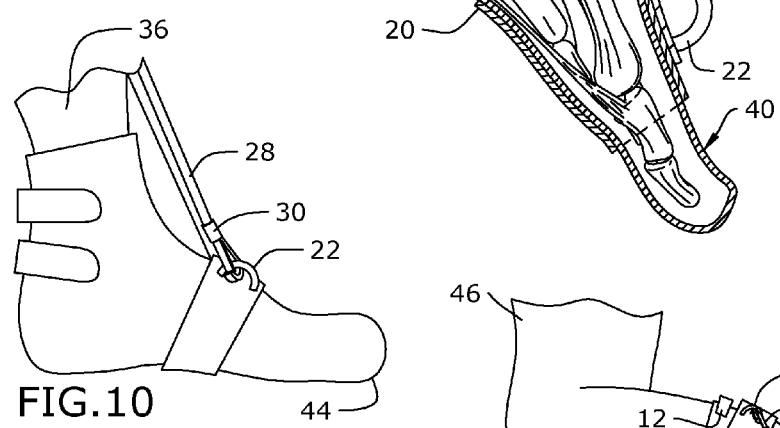
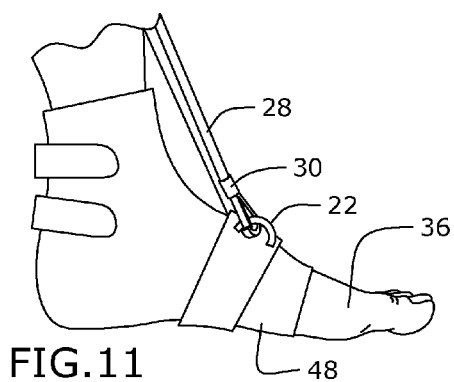
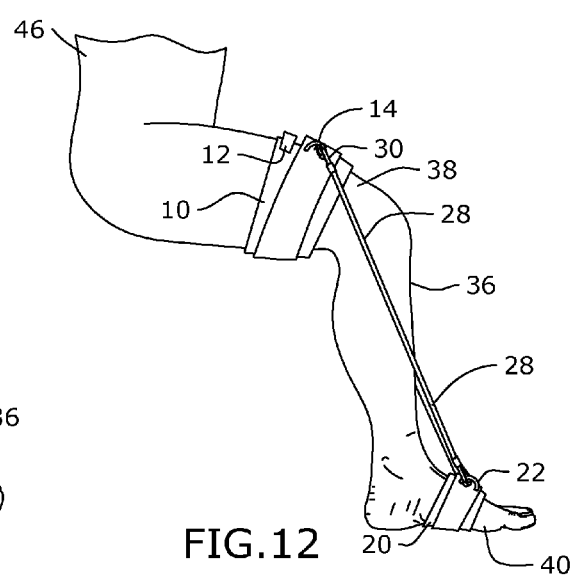

us 10,322,022 B2

PLANTAR FASCIITIS TREATMENT METHOD AND DEVICE

BACKGROUND OF THE INVENTION

The present invention relates to a treatment method and device and, more particularly, to a method and device that treats plantar fasciitis.

Plantar fasciitis, also known as plantar fasciitis or jogger's heel, is a disorder that results in pain in the heel and bottom of the foot. The pain is usually most severe with the first steps of the day or following a period of rest. Pain is also frequently brought on by bending the foot and toes up towards the shin and may be worsened by a tight Achilles tendon. The condition typically comes on slowly. In about a third of people both sides are affected.

As can be seen, there is a need for a device that treats and cures plantar fasciitis.

SUMMARY OF THE INVENTION

In one aspect of the present invention, a device for treatment of plantar fasciitis comprises: a foot strap comprising an inner surface and an outer surface, wherein the inner surface is sized to secure around a foot of a user in between an ankle and toes; a thigh strap comprising an inner surface and an outer surface, wherein the inner surface is sized to secure around a thigh of the user; and at least one resistance band having a first end and a second end, wherein the first end is attached to the foot strap and the second end is attached to the thigh strap.

In another aspect of the present invention, a method of treating plantar fasciitis comprising: securing a thigh strap around a thigh; securing a foot strap around a foot in between a heal and toes; attaching a first end of a resistance band to the foot strap and a second end of the resistance band to the thigh strap; and bending the foot downwards and curling the toes against the resistance of the band.

These and other features, aspects and advantages of the present invention will become better understood with reference to the following drawings, description and claims.

BRIEF DESCRIPTION OF THE DRAWINGS

FIG. 2 is a top perspective view of an embodiment of a thigh strap of the present invention;

FIG. 3 is a bottom perspective view of the thigh strap of FIG. 2;

FIG. 4 is a top perspective view of an embodiment of a foot strap of the present invention;

FIG. 5 is a bottom perspective view of the foot strap of FIG. 4;

FIG. 6 is a side view of an embodiment of the present invention shown in use;

FIG. 7 is a side view of an embodiment of the present invention shown in use in plantar flexion;

FIG. 8 is a section detail view of the present invention in use taken along line 8-8 in FIG. 6;

FIG. 9 is a section detail view of the present invention in use taken along line 9-9 in FIG. 7;

FIG. 10 is a perspective view of an embodiment of the present invention;

FIG. 11 is a perspective view of an embodiment of the present invention; and

FIG. 12 is a perspective view of an embodiment of the present invention.

DETAILED DESCRIPTION OF THE INVENTION

Figure 1:
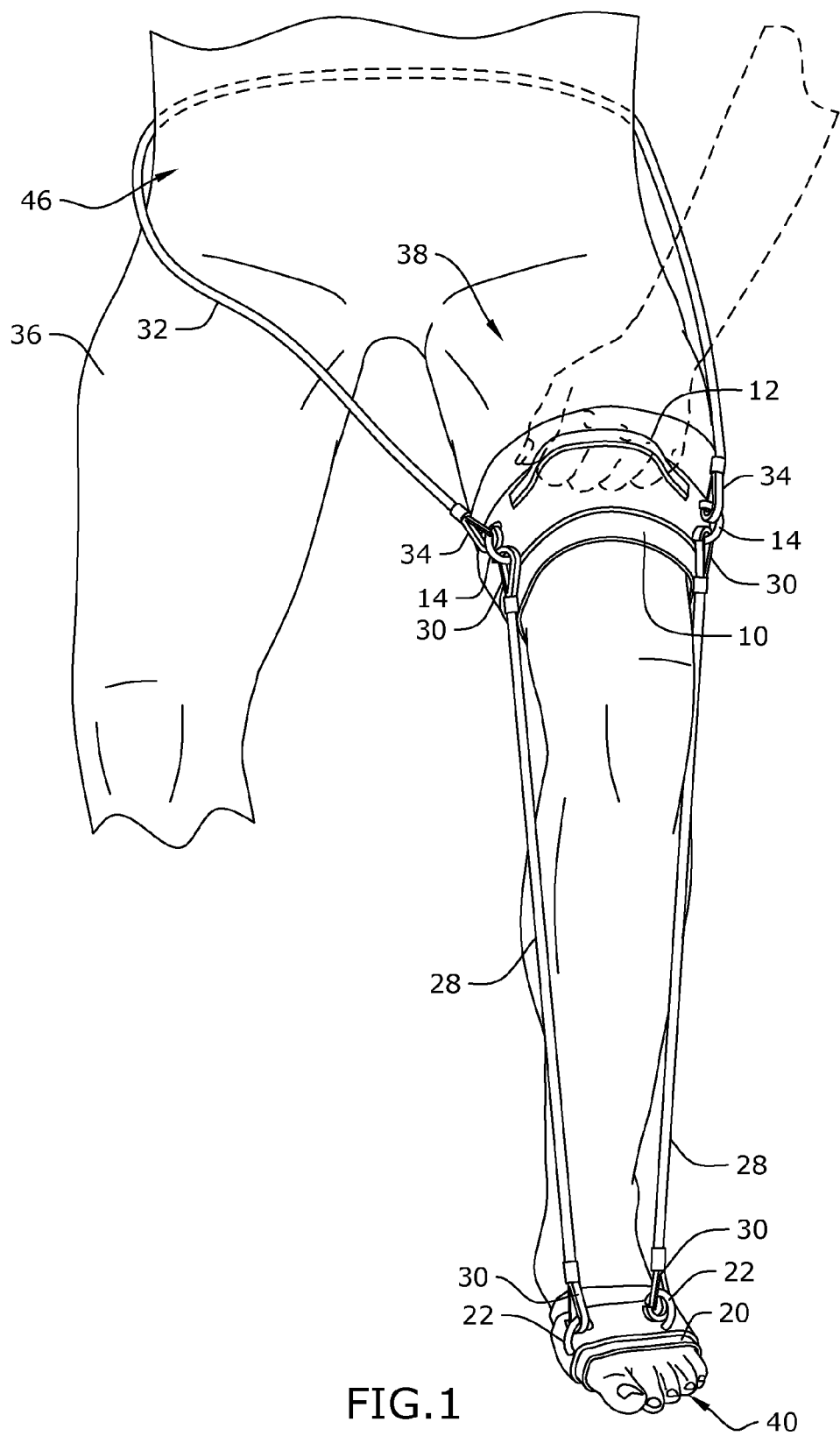
FIG. 1 is a perspective front view of an embodiment of the present invention shown in use.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Referring to FIGS. 1 through 12, the present invention includes a device for treatment of plantar fasciitis. Broadly, the device includes a foot strap 20, a thigh strap 10 and a resistance band 28. The foot strap 20 includes an inner surface and an outer surface. The inner surface of the foot strap 20 is sized to secure around a foot 40 of a user 36 in between the ankle and toes. The thigh strap 10 also includes an inner surface and an outer surface. The inner surface of the thigh strap 10 is sized to secure around a thigh 38 of the user 36. The resistance band 28 includes a first end attached to the foot strap 20 and a second end attached to the thigh strap 10. To treat the plantar fascia 42, the user 36 bends their foot 40 downwards against the resistance of the resistance band 28.

The foot strap 20 and the thigh strap 10 may be made of a bendable material, such as a fabric and the like so that the foot strap 20 and the thigh strap 10 are able to wrap around the foot 40 and the thigh 38 respectively. In certain embodiments, the foot strap 20 and the thigh strap 10 are connected to themselves by connectors 16, 18, 24, 26. The connectors 16, 18, 24, 26 may include hook and loop fasteners, snap buttons, clips, bands, male and female connectors and the like. Therefore, the foot strap 20 and the thigh strap 10 may be wrapped around and secured to the foot 40 and thigh 38.

As illustrated in FIGS. 2 and 3, the thigh strap 10 may be formed of a substantially flat material. The flat material is able to wrap around the thigh 38 of the user 36. In certain embodiments, the flat material may include a wide portion and a narrow portion. The wide portion may include a handle 12 and a first connector 16 secured to the outer surface. The narrow portion may include a first D-loop 14 and a second D-loop 14 secured to the outer surface, and a second connector 18 secured to the inner surface. The D-loops 14 may be made of a looped metal and may be sewn to the flat material. A user may place the inner surface of the wide portion on top of their thigh 38 and wrap the narrow portion around the leg and connect the second connector 18 to the first connector 16. The D-loops 14 and the handle 12 may thereby be disposed on the top of the thigh 38.

As illustrated in FIGS. 4 and 5, the foot strap 20 may be formed of a substantially flat material. The flat material is able to wrap around the foot 40 of the user 36 in between the toes and the ankle. In certain embodiments, the flat material may include a wide portion and a narrow portion. The wide portion may include a first connector 24 secured to the outer surface. The narrow portion may include a first D-loop 22 and a second D-loop 22 secured to the outer surface, and a second connector 26 secured to the inner surface. The D-loops 22 may be made of a looped metal and may be sewn to the flat material. A user may place the inner surface of the wide portion on top of their foot 36 and wrap the narrow portion around the foot and connect the second connector 26 to the first connector 24. The D-loops 22 may thereby be disposed on the top of the foot 36.

As mentioned above, the present invention utilizes at least one resistance band 28. The resistance band 28 is a typical workout resistance band that is formed of an elastic and stretchable material. Therefore, the resistance band 26 returns to its original length after being stretched. The resistance band 28 may be formed of a stretchable polymer, such as rubber, neoprene, and the like. In certain embodiments, the present invention may include two resistance bands 28. Each resistance band 28 may have a clip 30 secured to the first end and the second end. The first end of the first resistance band 28 secures to one of the D-loops 22 of the foot strap 20 via one of the clips 30 and the second end of the first resistance band 28 secures to one of the D-loops 14 of the thigh strap 10 via the other clip 30. The first end of the second resistance band 28 secures to the other D-loop 22 of the foot strap 20 via one of the clips 30 and the second end of the second resistance band 28 secures to the other D-loop 14 of the thigh strap 10 via the other clip 30. The first resistance band 28 and a second resistance band 28 are secured to the foot strap 20 and the thigh strap 10 such that the knee of the user 36 is disposed in between the first resistance band 28 and the second resistance band 28 when the device is worn by a user 36.

The present invention may further include a waist band 32. The waist band 32 is sized to wrap around a waist 46 of the user 36. A first end and a second end of the waist band 32 may each include clips 34. The clip 34 of the first end of the waist band 32 is releasably attached to the first D-loop 14 of the thigh strap 40 and the clip 34 of the second end of the waist band 32 is releasably attached to the second D-loop 14 of the thigh strap 40. Since the waist band 32 is wrapped around the user's waist 32, the thigh strap 40 may be prevented from sliding off of the user's thigh 38.

The foot strap 20 of the present invention may include any foot wear that secured around the foot 36 of the user. For example, as illustrated in FIG. 10, the foot strap 20 may be a boot 44. The D-loops 22 may be directly secured to the boot 44. In certain embodiments, the present invention may include an open toe boot 48.

The present invention further includes a method of treating the plantar fascia 42. The method includes securing the thigh strap 20 around the thigh 38; securing the foot strap 10 around the foot 40 in between a heal and toes; attaching a first end of the resistance band 28 to the foot strap 10 and a second end of the resistance band 28 to the thigh strap 20; wrapping a waist band 32 around the waist 46; attaching a first end of the waist band 32 to the thigh strap 10 and a second end of the waist band 32 to the thigh strap 10; and bending the foot downwards and curling the toes against the resistance of the resistance band 28. The user 36 may bend the foot downwards and curl the toes for a few sessions. The repetitive movement increases strength on plantar foot muscles (specifically the flexor digitorum longus and the flexor hallucis longus, responsible for curling toes) and soft tissue structures, improving stability, healing plantar fascia microtears and finally decreasing or eliminating pain.

It should be understood, of course, that the foregoing relates to exemplary embodiments of the invention and that modifications may be made without departing from the spirit and scope of the invention as set forth in the following claims.

What is claimed is:

1. A device for treatment of plantar fasciitis comprising:
a looped foot strap comprising an inner surface and an outer surface, wherein the inner surface is configured to secure around a foot of a user in between an ankle and toes;
a looped thigh strap comprising an inner surface and an outer surface, wherein the inner surface is configured to secure around a thigh of the user above a knee; and
a first elastic resistance band and a second elastic resistance band each secured to the looped foot strap at a first position corresponding to a top of the foot and the thigh strap, at a second position corresponding to an outer portion of the thigh, so that the first elastic resistance band and the second elastic resistance band angle towards each other running from the second position to the first position, and a knee of the user is disposed in between the first elastic resistance band and the second elastic resistance band when the device is worn by a user.

2. The device of claim 1, wherein the looped foot strap comprises a substantially flat material operable to wrap around the foot of the user.

3. The device of claim 1, wherein the inner surface of the looped foot strap comprises a first connector and the outer surface of the looped foot strap comprises a second connector releasably attached to the first connector.

4. The device of claim 1, wherein the looped thigh strap comprises a substantially flat material operable to wrap around the thigh of the user.

5. The device of claim 1, wherein the inner surface of the looped thigh strap comprises a first connector and the outer surface of the thigh strap comprises a second connector releasably attached to the first connector.

6. The device of claim 1, wherein the outer surface of the looped foot strap comprises a first pair looped materials and the outer surface of the thigh strap comprises a second pair of looped materials.

7. The device of claim 6, wherein first ends of the first and second elastic resistance bands each comprises a clip releasably attached to the first pair of looped materials of the looped foot strap and second ends of the first and second elastic resistance bands each comprises a clip releasably attached to the second pair of looped materials of the thigh strap.

8. The device of claim 1, further comprising a handle secured to the outer surface of the thigh strap.

9. The device of claim 1, further comprising a waist band having a first end attached to the thigh strap and a second end attached to the thigh strap, wherein the waist band is sized to fit around a waist of the user.

10. A method of treating plantar fasciitis comprising:
securing a looped thigh strap around a thigh and above a knee;
securing a looped foot strap around a foot in between a heal and toes;
attaching a first end of a first an elastic resistance band and a second elastic resistance band to the looped foot strap at a first position corresponding to a top of the foot and a second end of the first elastic resistance band and a second elastic resistance band to the looped thigh strap at a second position corresponding to an outer portion of the thigh so that the first elastic resistance band and the second elastic resistance band angle towards each other running from the second position to the first position; and
bending the foot downwards and curling the toes against the resistance of the elastic resistance band.

11. The method of claim 10, further comprising the steps of:
- wrapping a waist band around a waist; and
- attaching a first end of the waist band to the looped thigh strap and a second end of the waist band to the looped thigh strap.

* * * * *